United States Patent [19]

Abe et al.

[11] Patent Number: 5,296,631

[45] Date of Patent: Mar. 22, 1994

[54] PROCESS FOR PRODUCING N-ALKYL-N-METHYLAMINE OR N-ALKENYL-N-METHYLAMINE

[75] Inventors: Hiroshi Abe, Albany, Calif.; Hideki Taniguchi, Wakayama, Japan; Yoshifumi Nishimoto, Wakayama, Japan; Kohshiro Sotoya, Wakayama, Japan

[73] Assignee: Kao Corporation, Tokyo, Japan

[21] Appl. No.: 871,541

[22] Filed: Apr. 21, 1992

[30] Foreign Application Priority Data

Apr. 22, 1991 [JP] Japan .................................. 3-90270

[51] Int. Cl.$^5$ ........................................... C07C 209/16
[52] U.S. Cl. .................................... 564/480; 564/463; 564/509
[58] Field of Search ..................... 564/480, 463, 509

[56] References Cited

U.S. PATENT DOCUMENTS

| | | | |
|---|---|---|---|
| 3,708,539 | 1/1973 | Fenton | 564/480 |
| 4,014,933 | 3/1977 | Boettger et al. | 564/480 |
| 4,152,353 | 5/1979 | Habermann | 564/480 |
| 4,254,060 | 3/1981 | Kimura | 564/480 |
| 4,772,750 | 9/1988 | Habermann | 564/480 |
| 4,792,622 | 12/1988 | Yokota et al. | 564/473 |

FOREIGN PATENT DOCUMENTS 312253 4/1989 European Pat. Off. ............ 564/480

Primary Examiner—Glennon H. Hollrah
Assistant Examiner—Scott C. Rand
Attorney, Agent, or Firm—Birch, Stewart Kolasch & Birch

[57] ABSTRACT

A process for producing an N-alkyl-N-methylamine or an N-alkenyl-N-methylamine in a high yield from a higher alcohol and methylamine comprising the step of reacting a higher alcohol with methylamine in the presence of a catalyst comprising copper and a fourth period transition metal of the Periodic Table, except for chromium, or a catalyst comprising copper, a fourth period transition metal of the Periodic Table, except for chromium, and an element of the platinum group VIII of the Periodic Table, at a pressure ranging from atmospheric pressure to 100 atm. G., at a reaction temperature ranging from 100° to 250° C., with hydrogen gas being introduced into the reaction system while water produced in the reaction is removed from the reaction system and the amount of methylamine in the gaseous mixture which contains no matter formed through the reaction and is exhausted from the reaction system is regulated from 5 to 50% by volume.

9 Claims, No Drawings

PROCESS FOR PRODUCING N-ALKYL-N-METHYLAMINE OR N-ALKENYL-N-METHYLAMINE

BACKGROUND OF THE INVENTION

1. Field of the Invention

The present invention relates to a process for producing an N-alkyl-N-methylamine or an N-alkenyl-N-methylamine.

Aliphatic amines produced from tallow, coconut oil or palm oil are important intermediates for household and industrial products. Particularly aliphatic secondary amines such as N-alkyl-N-methylamine and N-alkenyl-N-methylamine are converted into quaternary ammonium salts and the like, and widely used as a raw material for softeners and antistatic agents and as a base material for conditioners.

2. Description of the Related Art

Aliphatic secondary amines have been produced from a fatty acid via a nitrile or by a process wherein a higher alcohol is aminated (see U.S. Pat. No. 4,792,622). Although only secondary amines having symmetrical alkyl chains (two alkyl chains which are identical with each other) can be produced in the former process, secondary amines having asymmetrical alkyl chains can be obtained by reacting a long-chain alcohol with a long-chain primary amine in the latter process (see Japanese Patent Laid-Open No. 202854/1990). However, even by the latter process, an efficient production of an N-(long-chain alkyl)-N-methylamine wherein one of the alkyl chains is a methyl group is difficult, because an N,N-di(long-chain alkyl)-N-methylamine is formed in a large amount as a by-product.

DISCLOSURE OF THE INVENTION

Summary of the Invention

An object of the present invention is to provide a process for producing an aliphatic secondary amine, i.e. N-alkyl-N-methylamine or N-alkenyl-N-methylamine, in a high yield from a higher alcohol and methylamine.

After intensive investigations, the inventors have found that the efficient production of an N-(long-chain alkyl)-N-methylamine can be achieved by reacting a higher alcohol with methylamine under strictly specified conditions. The present invention has been completed on the basis of this finding.

Thus the present invention provides a process for producing an N-alkyl-N-methylamine or an N-alkenyl-N-methylamine, which comprises or essentially consists the step of reacting a higher alcohol with methylamine in the presence of a catalyst comprising or essentially consisting of copper and a fourth period transition metal of the Periodic Table, except for chromium, or a catalyst comprising or essentially consisting of copper, a fourth period transition metal of the Periodic Table, except for chromium, and an element of the platinum group VIII of the Periodic Table, at a pressure ranging from atmospheric pressure to 100 atm. G., at a reaction temperature ranging from 100° to 250° C., with hydrogen gas being introduced into the reaction system while water produced in the reaction is removed from the reaction system and the amount of methylamine in the gaseous mixture which contains no matter formed through the reaction and is exhausted from the reaction system is regulated from 5 to 50% by volume.

The higher alcohol is preferably a straight-chain or branched, saturated or unsaturated aliphatic alcohol having 8 to 36 carbon atoms, still more preferably one having 12 to 18 carbon atoms.

The catalyst is preferably one comprising copper, a fourth period transition metal of the Periodic Table, except for chromium, and an element of the platinum group VIII of the Periodic Table, in a weight ratio of 0.1–10/1/0–0.5, in terms of metal atom.

The catalyst is preferably one comprising copper, zinc and ruthenium or copper, zinc and palladium.

The catalyst is preferably present in an amount of 0.1 to 10% by weight, based on the weight of the higher alcohol.

The hydrogen gas is preferably introduced in an amount of 10 to 50 $cm^3$/hr, per gram of the higher alcohol.

Further scope and the applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

DETAILED DESCRIPTION OF THE INVENTION

The catalyst to be used in the present invention comprises copper and a fourth period transition metal of the Periodic Table, except for chromium, which may optionally contain an element of the platinum group VIII of the Periodic Table. The fourth period transition metal of the Periodic Table used herein includes scandium (Sc), titanium (Ti), vanadium (V), manganese (Mn), iron (Fe), cobalt (Co), nickel (Ni), copper (Cu) and zinc (Zn). The fourth period transition metal of the Periodic Table used herein is preferably one or more metals selected from the group consisting of nickel, cobalt and zinc, particularly and preferably zinc. The element of the platinum group VIII of the Periodic Table includes iron (Fe), cobalt (Co), nickel (Ni), ruthenium (Ru), rhodium (Rh), palladium (Pd), osmium (Os), iridium (Ir) and platinum (Pt). The element of the platinum group VIII of the Periodic Table used herein is preferably one or more metals selected from the group consisting of platinum, palladium and ruthenium, particularly and preferably palladium or ruthenium.

As for the weight ratio of the metal atoms in the catalyst used in the present invention, the weight ratio of copper, the fourth period transition metal of the Periodic Table (excluding Cr) and the element of the platinum group VIII of the Periodic Table is preferably 0.1–10/1/0–0.5. Beyond this range, an efficient production of the N-alkyl-N-methylamine or the N-alkenyl-N-methylamine according to the present invention tends to be impossible.

The catalyst according to the present invention can be in various forms. The effect due to the interaction of the components can be obtained only when a catalyst comprising two components, i.e. copper and a fourth period transition metal of the Periodic Table (excluding Cr), or three components, i.e. copper, a fourth period transition metal of the Periodic Table (excluding Cr) and an element of the platinum group VIII of the Periodic Table, is present in the reaction system. These combinations thus exhibit an essential catalytic function, and the catalytic activity can be exhibited in the reaction of the higher alcohol, methylamine and hydrogen only after the catalyst is activated. Thus a difference in the form of the metals before the activation and after the activation in the reaction system is not particularly limited. It will suffice when the catalytic effect of copper and the fourth period transition metal of the Periodic Table (excluding Cr) or that of copper, the fourth period transition metal of the Periodic Table (excluding Cr) and the element of the platinum group VIII of the Periodic Table is exhibited after the activation.

The catalyst used in the present invention can be activated by reduction using a reducing agent such as hydrogen gas, aqueous solution of formaldehyde and sodium borohydride.

The forms of the metals usable as the catalyst in the process of the present invention are as follows:

(1) those dispersible in the reaction medium, such as the metals per se, oxides or hydroxides of the metals, or a mixture of the metals per se, oxides and hydroxides of the metals.

(2) a mixture of supports carrying a metal, i.e., a mixture of copper carried on a suitable support and a fourth period transition metal of the Periodic Table (excluding Cr) carried on a suitable support, or a mixture of copper carried on a suitable support, a fourth period transition metal of the Periodic Table (excluding Cr) carried on a suitable support and an element of the platinum group VIII of the Periodic Table carried on a suitable support, or a support uniformly carrying a mixture of metals which comprises copper and a fourth period transition metal of the Periodic Table (excluding Cr), or copper, a fourth period transition metal of the Periodic Table (excluding Cr) and an element of the platinum group VIII of the Periodic Table. They can be dispersed in the reaction medium.

(3) those that form a metallic colloid in the reaction medium to give a homogeneous system, such as aliphatic carboxylic acid salts of the above-described metals and complexes of the above-described metals stabilized with a suitable ligand.

(4) a mixture of the metals in such a form that they are dispersible in the reaction medium, e.g. the form (1) or (2), with the metals capable of forming a homogeneous system in the reaction medium, e.g. the form (3), or metals which are a form of a dispersion prior to the activation and which are in the form of a homogeneous system after the activation.

The metals in any of these forms can be used as long as the two or three indispensable components of the catalyst system used in the present invention exhibit the catalytic effect after activation. From the viewpoint of the stabilization of the catalytic metals, namely, the fixation of the active surface and the resistance to catalyst poisoning, a preferred form of the catalyst to be used in the present invention is one obtained by uniformly carrying the above-described metal components on a suitable support.

In order to carry the two or three metal components, i.e., copper and a fourth period transition metal of the Periodic Table (excluding Cr), or copper, a fourth period transition metal of the Periodic Table (excluding Cr) and an element of the platinum group VIII of the Periodic Table on a support, the supports usable herein are those ordinarily used as a catalyst support such as alumina, silica/alumina, magnesia, titania, diatomaceous earth, silica, active carbon, and natural and synthetic zeolites. The amount of the catalytic metals to be carried on the support is not particularly limited. It is usually preferably 5 to 70% by weight based on the weight of the support.

The method of carrying the two or three metal components on the support surface can also be selected from various methods. The form of the starting catalytic metals may be oxides, hydroxides or various salts of copper, the fourth period transition metal of the Periodic Table (excluding Cr) and the element of the platinum group VIII of the Periodic Table. They include chlorides, sulfates, nitrates, acetates and aliphatic carboxylic acid salts of copper, the fourth period transition metal of the Periodic Table (excluding Cr) and the element of the platinum group VIII of the Periodic Table. Further complexes of these metals, such as acetylacetone complexes and dimethylglyoxime complexes of copper, the fourth period transition metal of the Periodic Table (excluding Cr) and the element of the platinum group VIII of the Periodic Table are also usable. In addition, a carbonyl complex, amine complex or phosphine complex of the element of the platinum group VIII of the Periodic Table can also be used.

When the catalyst is produced by carrying the metals on the support by using these starting metal materials, any known process can be employed such as a process which comprises putting the support in a solution of suitable salts of copper, the fourth period transition metal of the Periodic Table (excluding Cr) and the element of the platinum group VIII of the Periodic Table to sufficiently impregnate the support with the solution, followed by drying and firing. Another process comprises either mixing the support thoroughly with an aqueous solution of suitable salts of copper, the fourth period transition metal of the Periodic Table (excluding Cr) and the element of the platinum group VIII of the Periodic Table and adding an aqueous alkali solution such as sodium carbonate aq. soln., sodium hydroxide aq. soln. and aqueous ammonia thereto to precipitate the metal salts on the support or, alternatively, adding an aqueous solution of suitable salts of copper, the fourth period transition metal of the Periodic Table (excluding Cr) and the element of the platinum group VIII of the Periodic Table, and an aqueous alkali solution such as sodium carbonate aq. soln., sodium hydroxide aq. soln. and aqueous ammonia to an aqueous slurry of the support at once in such a manner that the slurry has a constant pH value (for example, 7) to precipitate the metal salts on the support, followed by drying and firing. Thus, a catalyst of copper/fourth period transition metal of the Periodic Table (excluding Cr) or a catalyst of copper/fourth period transition metal of the Periodic Table (excluding Cr)/element of the platinum group VIII of the Periodic Table is obtained.

Another process is also effective wherein only copper or only copper and the fourth period transition metal of the Periodic Table (excluding Cr) are carried on a support and, prior to the reaction, the element of the platinum group VIII of the Periodic Table carried on a support, an aliphatic carboxylic acid salt thereof or complex thereof is added thereto to form a composite of copper, the fourth period transition metal of the Periodic Table (excluding Cr) and the element of the platinum group VIII of the Periodic Table. A still preferred catalyst form is such that the two or three components of the catalyst are homogeneously carried on one and the same support. The two or three components, i.e. copper and the fourth period transition metal of the Periodic Table (excluding Cr), or copper, the fourth period transition metal of the Periodic Table (excluding Cr) and the element of the platinum group VIII of the Periodic Table, are essentially indispensable in the catalyst used in the present invention.

The amount of the catalyst used in the present invention is 0.1 to 10% by weight based on the weight of the higher alcohol.

The higher alcohol to be used as the starting material in the present invention is a straight-chain or branched, saturated or unsaturated aliphatic alcohol having 8 to 36 carbon atoms, for example, an alcohol having a straight-chain, such as octyl alcohol, lauryl alcohol, myristyl alcohol, stearyl alcohol, behenyl alcohol, oleyl alcohol and a mixture thereof; and an alcohol having a branch chain, such as Fine Oxocohol 180 and 180N (products of Nissan Chemical Industries, Ltd.), Diadol 18G (a product of Mitsubishi Chemical Industries Ltd.) and Dobanol 23-I (a product of Mitsubishi Petrochemical Co., Ltd.).

In the present invention, the pressure and temperature in the reaction system must be controlled to be in the range of atmospheric pressure to 100 atm. G. and 100° to 250° C., respectively. When the pressure and/or temperature are outside these ranges, the object of the present invention cannot be attained.

In the present invention, it is necessary that hydrogen gas is blown into the reaction system during the reaction while removing water formed by the reaction, from the reaction system. Water may be removed from the reaction system either continuously or intermittently.

In the present invention, the catalyst previously reduced with hydrogen gas and the like is used or, alternatively, an unreduced catalyst is put into the reactor together with the starting higher alcohol and they are heated to the reaction temperature while blowing hydrogen gas thereinto to reduce the catalyst. The amount of hydrogen gas to be introduced is 1 to 100 cm$^3$/hr, preferably 10 to 50 cm$^3$/hr, per gram of the starting higher alcohol.

It is important in the present invention to regulate the content of methylamine in the gaseous mixture containing no matter formed through the reaction (hereinafter referred to as the exhaust gas), which is freed from the formed water and is exhausted from the reaction system, to 5 to 50% by volume, preferably 10 to 30% by volume based on the entire exhaust gas. When this condition is not satisfied, the object of the present invention cannot be attained. The regulation of the content of methylamine in the exhaust gas is conducted, for example, by controlling the blown rate of the methylamine gas to the reaction system. Namely, as increasing the blown rate of the methylamine gas, the content of methylamine in the exhaust gas is increased, and the decrease of the blown rate of the methylamine gas causes the reduction of the content of methylamine in the exhaust gas. The determination of methylamine in the exhaust gas is conducted by gas chromatography.

The description will now be made as to a preferred embodiment of the process of the present invention.

The starting higher alcohol and the catalyst are fed into a reactor provided with a inlet tube for hydrogen gas and nitrogen gas and a rectification column. Although the amount of the catalyst is not particularly limited, it is usually in the range of 0.1 to 10% by weight based on the weight of the feed alcohol.

In order to reduce the catalyst in the reaction system, the air in the reaction system is purged with nitrogen gas, the reactor is heated to the reduction temperature while blowing hydrogen gas thereinto and maintained at this temperature for 0.5 to 3 hours. The reduction is conducted usually at 160° to 250° C. After the completion of the reduction of the catalyst, the reaction temperature and the reaction pressure are fixed at predetermined ones. The reaction temperature is 100° to 250° C. and the reaction pressure is atmospheric pressure to 100 atm. G. Then hydrogen gas is blown into the reactor at a given flow rate. The flow rate is 1 to 100 cm$^3$/hr per gram of the higher alcohol.

Then methylamine gas is blown into the reactor to start the reaction. The amount of methylamine gas to be blown is such that the content thereof in the exhaust gas will be 5 to 50% by volume. The content of methylamine in the exhaust gas is quantified by gas chromatography. The reaction is completed when the amount of the remaining starting alcohol has been reduced to 1% or less as determined by following the reaction by gas chromatography. After the completion of the reaction, the catalyst is removed by filtration and the product is purified by distillation to obtain the N-alkyl-N-methylamine or the N-alkenyl-N-methylamine.

According to the process of the present invention, the N-alkyl-N-methylamine or the N-alkenyl-N-methylamine can be highly, efficiently obtained.

EXAMPLES

The following Examples will further illustrate the present invention, which by no means limit the present invention.

Processes for producing the catalysts used in the following Examples are summarized below.

Production of the catalyst

A copper/nickel catalyst (catalyst A), a copper/zinc catalyst (catalyst B), a copper/zinc/ruthenium catalyst (catalyst C), a copper/cobalt/palladium catalyst (catalyst D) and a copper/nickel/platinum catalyst (catalyst E) which were supported on a synthetic zeolite were produced as described below.

(1) Catalyst A

A synthetic zeolite was fed into a 1-l flask. Then copper nitrate and nickel nitrate were dissolved in water in such amounts that the weight ratio of the metal atoms (Cu:Ni) would be 4:1, and the obtained aqueous mixture was poured into the flask and heated while stirring. A 10% aqueous Na$_2$CO$_3$ solution was slowly dropped into the resulting solution at 90° C. After aging for 1 hour, the precipitates were separated by filtration, washed with water, dried at 100° C. for 10 hours, and then fired at 600° C. for 3 hours. The amount of the metal oxides thus carried was 50% by weight based on the support.

(2) Catalyst B

Titania was fed into a 1-l flask. Then copper nitrate and zinc nitrate were dissolved in water in such amounts that the weight ratio of the metal atoms (Cu:Zn) would be 5:1, and the obtained aqueous mixture was poured into the flask and heated while stirring. A 10% aqueous Na$_2$CO$_3$ solution was slowly dropped into the resulting solution at 90° C. After aging for 1 hour, the precipitates were separated by filtration, washed with water, dried at 100° C. for 10 hours, and then fired at 600° C. for 3 hours. The amount of the metal oxides thus carried was 50% by weight based on the weight of the support.

(3) Catalyst C

A synthetic zeolite was fed into a 1-l flask. Then copper nitrate, zinc nitrate and ruthenium chloride were dissolved in water in such amounts that the weight ratio of the metal atoms (Cu:Zn:Ru) would be 4:1:0.01, and the obtained aqueous mixture was poured into the flask and heated while stirring. A 10% aqueous Na₂CO₃ solution was slowly dropped into the resulting solution at 90° C. After aging for 1 hour, the precipitates were separated by filtration, washed with water, dried at 100° C. for 9 hours, and then fired at 600° C. for 1 hour. The amount of the metal oxides thus carried was 50% by weight based on the support.

(4) Catalyst D

Alumina was fed into a 1-l flask. Then copper nitrate, cobalt nitrate and palladium chloride were dissolved in water in such amounts that the weight ratio of the metal atoms (Cu:Co:Pd) would be 2:1:0.1, and the obtained aqueous mixture was poured into the flask and heated to 90° C. under stirring under reduced pressure to evaporate water. The residue was fired at 400° C. for 3 hours. The amount of the metal oxides thus carried was 20% by weight based on the weight of the support.

(5) Catalyst E

Diatomaceous earth was put into a 1-l flask. Then copper nitrate, nickel nitrate and palladium chloride were dissolved in water in such amounts that the weight ratio of the metal atoms (Cu:Ni:Pd) would be 9:1:0.001, and the obtained aqueous mixture was poured into the flask and heated to 90° C. under stirring under reduced pressure to evaporate water. The residue was fired at 400° C. for 3 hours. The amount of the metal oxides thus carried was 20% by weight based on the weight of the support.

EXAMPLE 1 AND COMPARATIVE EXAMPLE 1

1200 g of stearyl alcohol (Kalcohl-80; a product of Kao Corporation) and 6 g (0.5% by weight based on the starting alcohol) of the catalyst A were put into a 2-l separable flask. The air in the vessel was purged with nitrogen gas and heating was started under stirring. When the temperature of the contents in the vessel reached 100° C., the blowing of hydrogen gas into the reaction system at a flow rate of 40 l/hr with a flowmeter was started, and then the temperature was elevated to the reaction initiation temperature of 190° C. Methylamine gas was blown thereinto at that temperature so that the methylamine content in the exhaust gas would be 20% by volume to initiate the reaction. The reaction was conducted under atmospheric pressure until the amount of the remaining starting alcohol was reduced to 1% by weight or less. The amount of the remaining alcohol and the composition of the reaction product obtained after the completion of the reaction were determined by gas chromatography. As a result, the intended secondary amine (N-stearyl-N-methylamine) was obtained in a yield of 85%.

In Comparative Example 1, the same procedure as that of the Example 1 was repeated except that Cu-Cr catalyst (a product of Nikki Chemical Co., Ltd.) was used. N-stearyl-N-methylamine was obtained in a yield of 51%.

EXAMPLES 2 TO 5 AND COMPARATIVE EXAMPLE 2

The same procedure as that of the Example 1 was repeated except that a branched alcohol represented by the formula:

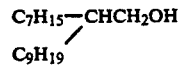

(Diadol 18G; a product of Mitsubishi Chemical Industries Ltd.) was used, the reaction temperature was altered to 210° C. and the catalyst B, C, D or E was used as the catalyst.

In Comparative Example 2, the same procedure as that of the Example 3 was repeated except that the feed of methylamine was conducted at a predetermined flow rate (40 l/hr) (as a result, the methylamine content in the exhaust gas was 5 to 90% by weight). The results are given in Table 1.

TABLE 1

| | Catalyst | Methylamine content in the exhaust gas (vol. % based on the entire exhaust gas) | Yield of N-alkyl-N-methylamine (GC %)*¹ |
|---|---|---|---|
| Ex. 2 | B | 20 | 87 |
| Ex. 3 | C | 20 | 93 |
| Ex. 4 | D | 20 | 91 |
| Ex. 5 | E | 20 | 89 |
| Comp. Ex. 2 | C | 5~90 | 51 |

(Note)
*¹The yield was less than 100%, since the N,N-di(long-chain alkyl)-N-methylamine was produced as a by-product.

It will be apparent from the results that the N-alkyl-N-methylamine can be produced in a high yield by the process of the present invention.

EXAMPLES 6 TO 8

The reaction was conducted in the same manner as that of the Example 3 except that 2-(3-methylhexyl)-7-methyl-1-decanol (Fine Oxocohol 180N, a product of Nissan Chemical Industries, Ltd.), a branched alcohol represented by the formula:

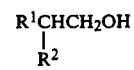

wherein R¹ is an alkyl group having 1 to 5 carbon atoms and R² is an alkyl group having 5 to 10 carbon atoms with a proviso that the total of the carbon number of R¹ and R² is 10 or 11 (Dobanol 23-I, a product of Mitsubishi Petrochemical Co., Ltd.) or lauryl alcohol (Kalcohl 20, a product of Kao Corporation) was used as the starting alcohol and the methylamine content in the exhaust gas was regulated as given in Table 2 to obtain a corresponding N-alkyl-N-methylamine. The results are given in Table 2.

TABLE 2

| | Starting alcohol | Methylamine content in the exhaust gas (vol. % based on the entire exhaust gas) | Yield of N-alkyl-N-methylamine (GC %)*¹ |
|---|---|---|---|
| Ex. 6 | Fine Oxocohol 180N | 10~30 | 94 |
| Ex. 7 | Dobanol 23-I | 10~30 | 90 |
| Ex. 8 | Kalcohl 20 | 10~30 | 84 |

(Note)
*¹The yield was less than 100%, since the N,N-di(long-chain alkyl)-N-methylamine was produced as a by-product.

It will be apparent from the results that the N-alkyl-N-methylamine can be produced in a high yield by the process of the present invention.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What we claim:

1. A process for producing an N-alkyl-N-methylamine or an N-alkenyl-N-methylamine, which comprises a step of reacting a higher alcohol with methylamine in the presence of: (1) a catalyst comprising copper and a fourth period transition metal of the Periodic Table, except for chromium, or (2) a catalyst comprising copper, a fourth period transition metal of the Periodic Table, except for chromium, and an element of the platinum group VIII of the Periodic Table, at a pressure ranging from atmospheric pressure to 100 atm. G., at a reaction temperature ranging from 100° to 250° C., with hydrogen gas being introduced into the reaction system while water produced in the reaction is removed from the reaction system and the amount of methylamine in a gaseous mixture that is exhausted from the reaction system and which contains no water formed through the reaction, is regulated from 5 to 50% by volume.

2. The process as claimed in claim 1, wherein the higher alcohol is a straight-chain or branched, saturated or unsaturated aliphatic alcohol having 8 to 36 carbon atoms.

3. The process as claimed in claim 1, wherein the higher alcohol is a straight-chain or branched, saturated or unsaturated aliphatic alcohol having 12 to 18 carbon atoms.

4. The process as claimed in claim 1, wherein said catalyst (1) comprises copper, a fourth period transition metal of the Periodic Table, except for chromium, in a weight ratio of 0.01-10/1 in terms of metal atom, and said catalyst (2) comprises copper, a fourth period transition metal of the Periodic Table, except for chromium, and an element of the platinum group VIII of the Periodic Table in a weight ratio of 0.01-10/1/0-0.5, in terms of metal atom.

5. The process as claimed in claim 1, wherein said catalyst (2) is one comprising copper, zinc and ruthenium or copper, zinc and palladium.

6. The process as claimed in claim 1, wherein said catalyst (1) or (2) is present in an amount of 0.1 to 10% by weight, based on the weight of the higher alcohol.

7. The process as claimed in claim 1, wherein hydrogen gas is introduced in an amount of 10 to 50 cm$^3$/hr, per gram of the higher alcohol.

8. The process as claimed in claim 1, wherein the higher alcohol is selected from the group consisting of octyl alcohol, lauryl alcohol, myristyl alcohol, stearyl alcohol, behenyl alcohol, oleyl alcohol and a mixture thereof.

9. The process as claimed in claim 1, which further comprises a catalyst support on which catalyst (1) or (2) is supported thereon.

* * * * *